United States Patent [19]
Levin et al.

[11] 3,962,107
[45] June 8, 1976

[54] ENZYME-CONTAINING DENTURE CLEANSER TABLET

[75] Inventors: Norman Arthur Levin, Somerville; Leonard Louis Kaplan, East Brunswick, both of N.J.

[73] Assignee: Johnson & Johnson, New Brunswick, N.J.

[22] Filed: June 24, 1974

[21] Appl. No.: 482,404

[52] U.S. Cl.................. 252/100; 252/95; 252/DIG. 12; 424/16; 424/50
[51] Int. Cl.² .......................... C11D 7/54
[58] Field of Search ...... 252/100, 95, 102, DIG. 12; 424/16, 44, 50

[56] References Cited
UNITED STATES PATENTS

| | | | |
|---|---|---|---|
| 3,243,377 | 3/1966 | Stolar et al. | 252/95 |
| 3,372,125 | 3/1968 | Hill | 424/50 |
| 3,607,759 | 9/1971 | Barth | 252/95 |
| 3,630,924 | 12/1971 | Miller | 252/100 |
| 3,696,188 | 10/1972 | Fernandez et al. | 424/16 |
| 3,723,327 | 3/1973 | Kampen et al. | 252/100 |

*Primary Examiner*—William E. Schulz

[57] ABSTRACT

A water-soluble effervescent, layered denture cleanser tablet containing one or more enzymes in one layer and one or more active oxygen compounds in the other layer and in which the enzyme layer is faster dissolving than the active oxygen layer and is substantially completely dissolved before the dissolution of the active oxygen layer reaches a level which would inactivate the enzyme.

5 Claims, No Drawings

ENZYME-CONTAINING DENTURE CLEANSER TABLET

BACKGROUND OF THE INVENTION

This invention relates to denture cleanser tablets and, more particularly, is directed to an improved completely water-soluble denture cleanser tablet containing enzymatic cleansing agents.

Denture cleanser tablets, in general, contain citric and tartaric acids and sodium bicarbonate, the interaction of of which generates carbon dioxide bubbles as the tablet dissolves when it is placed in water and thereby providing a mechanical cleansing action. Usually, to prevent the generated carbon dioxide bubbles from adhering to the dissolving tablet, they also contain an anti-foam silicone such as dimethyl polysiloxane thereby assuring that the tablet is continually acted upon by the water in which it is placed.

Denture cleanser tablets usually also have included therein one or more active oxygen compounds such as sodium perborate monohydrate, potassium persulfate, sodium carbonate peroxide, potassium peroxydiphosphate, diperisophthalic acid and the like, which cause the tablets to evolve micro-bubbles of active oxygen as they are dissolved in water and provide an oxidizing cleansing action. Generally, they also contain a surfactant to lower the surface tension and to enhance the cleansing action.

To form the dry active ingredients of the foregoing types into denture cleanser tablets of convenient size and compaction or of desired color and flavor, various other relatively inactive ingredients such as fillers, extenders, binders, colors or dyes and flavors, etc. are incorporated. Formulations for denture cleanser tablets also contain a lubricant system to facilitate smooth and even flow of the dry granular materials of the formulations during tabletting operations. In the past, such lubricant systems have generally been water insoluble substances such as magnesium stearate or talc; recently a more desirable water-soluble lubricant system consisting of an admixture of a spray dried magnesium lauryl sulfate powder and micronized polyethylene glycol polymer has been discovered and forms the subject matter of copending U.S. Application Ser. No. 482,403 filed June 24, 1974.

It has also been proposed in the past to include in denture cleanser tablets enzymatic cleansing agents to attack particularly the proteinaceous materials that are loosely bonded to the mucin and plaque that adhere to dentures in normal use. However, such enzymatic cleansing agents have not been usefully incorporated in denture cleanser formulations because of the inactivating effect of the active oxygen compounds on the enzyme during the shelf life period as well as in the water solution when the tablet is placed in water with the dentures to be cleaned.

Thus, it is apparent that a need exists for a denture cleanser tablet which will provide not only the usual cleansing abilities provided by the effervescence of carbon dioxide bubbles in water and the free active oxygen micro-bubbles but also an enzymatic cleansing action provided to attack the proteins, carbohydrates and fats that are loosely bound to the mucin and plaque adhering to dentures during normal use, and preferably to remove the plaque itself.

SUMMARY OF THE INVENTION

According to the present invention, there is provided a water-soluble, effervescent, layered denture cleanser tablet comprising an enzyme layer containing at least one enzyme in admixture with an effervescence producing mixture of an acid and an alkali metal carbonate compound and the second layer containing at least one active oxygen compound in the admixture with an effervescence producing mixture of an acid and an alkali metal carbonate compound; further, the tablet is formulated in such a manner that the enzyme containing layer is substantially completely dissolved before the amount of dissolution of the active oxygen layer reaches a level to inactivate the enzyme. Thus, in the tablet of the present invention each of the cleansing functions, namely, the enzymatic action, the oxidizing action of the active oxygen compound and the mechanical cleansing action provided by the effervescent carbon dioxide bubbles are usefully effective. Further, the tablet shows the property of complete water-solubility.

DETAILED DESCRIPTION OF THE INVENTION

The denture cleanser tablet of the present invention is layered. It is layered into a rapidly dissolving enzyme layer and a less rapidly dissolving active oxygen or oxidizing layer. By the separation of the enzymatic and active oxygen cleansing components provided by layering, the enzymatic cleansing component is not rendered ineffective during shelf-life. The provision for a faster dissolving enzyme layer permits enzymatic cleansing activity to proceed before the dissolution of the active oxygen layer reaches a level which would inactivate the enzyme. Each layer contains an effervescence producing composition which aids not only in the dissolution of the layers but provides a mechanical cleansing action.

In the layered denture cleanser tablets of the present invention, the enzyme layer contains at least one enzyme preferably one selected from the group consisting of protease, alkalase, amylase, lipase, dextranase and mutanase. The active oxygen layer contains at least one active oxygen compound preferably one selected from the group consisting of sodium perborate monohydrate, potassium persulfate, sodium carbonate peroxide, diperisophthalic acid and potassium peroxydiphosphate. The effervescence producing composition is a carbon dioxide generating mixture comprising a carbonate compound and an acid. By "carbonate compound" is meant an alkali metal carbonate or bicarbonate, such as carbonate or bicarbonate of sodium, potassium, lithium or rubidium. The acid component is preferably citric or tartaric acid or mixtures thereof but may be other acids including other acids and mixtures thereof such as for example sodium or potassium acid phosphates, gluconic acid, malic acid, etc. Each layer also includes a water-soluble binder, an antifoaming agent and a water-soluble lubricant. The enzyme containing layer may also include a dye and a flavor ingredient to render the layered effect visible to the eye and to impart a pleasing taste to the dentures being cleansed.

The faster dissolving property of the enzyme layer is made possible by a careful consideration of the relative thicknesses of the two layers, the proportion of the effervescence producing composition in each layer, and the particle size of certain ingredients in each layer, as will be more fully described hereinafter.

Water-soluble, effervescent denture cleanser tablets are made by first preparing and drying a granulation of the acid and the carbonate compound for each layer using a suitable binder in an anhydrous alcohol solution. The resulting granular mixture is then dried to a moisture content of 0.4% or less, screened, and then thoroughly blended with the desired active ingredients along with binders, fillers, extenders, dyes, flavors, lubricants and the like in a suitable blending apparatus. The final blends are fed into a punch and die tabletting press where it is compacted into tablets. Thereafter the tablets so formed are released and packaged. The enzyme containing layered denture cleanser tablet of the present invention assures not only the physical separation of the enzymes from the active oxygen compounds in the finished tablet, but also the separation of release times of the components at the situs of operation.

For purposes of illustration, preferred compositions for each layer are identified herein as Enzyme Formulation and Active Oxygen Formulation. To be incorporated in and be a component of the Enzyme Formulation and of the Active Oxygen Formulation there is prepared a granular effervescence producing composition, identified herein as Effervescent Formulation comprising an acid and an alkali metal carbonate compound, an antifoaming agent and a binder. The Effervescent Formulation to be employed in the Enzyme Formulation and in the Active Oxygen Formulation may be the same or different.

To prepare the Enzyme Formulation, one of the Effervescent Formulations is blended with an enzyme, a water-soluble lubricant system and optionally a flavoring and a dye. To prepare the Active Oxygen Formulation, a second Effervescent Formulation is blended with one or more active oxygen compounds, and a water-soluble lubricant system. The formulations are fed into separate hoppers of a two-layer tabletting machine to produce an inactivation-resistant enzyme-containing layered denture cleanser tablet.

In the granular Effervescent Formulation, the acid component is preferably citric or tartaric acid or a mixture thereof. The acid or acids are of pharmaceutical grade and may be employed in a powder or a granular form. The alkali metal carbonate or bicarbonate compound preferably is sodium bicarbonate or carbonate. For granulation, suitable binders include for example polyvinylpyrrolidone of K-values (Fikentscher's viscosity coefficient) in the range 26 to 32. A preferred antifoaming agent is dimethyl polysiloxane. Suitable solvents are anhydrous alcoholic solvents such as ethanol and isopropanol, conveniently in the commercially available forms such as specially denatured alcohol (S.D.A.), 3A alcohol 200 proof or anhydrous isopropanol.

The amount of the ingredients for the Effervescent Formulation may be varied over a relatively wide range. The amounts by weight based on the total weight of the Effervescent Formulation are as follows: The acid or acids may be present in from about 35 to 55 percent or at least in stoichiometric quantities with repsect to the carbonate compound. Preferred are mixtures of citric and tartaric acids and when employed, the citric acid is employed in amounts of from about 15 to about 25 percent and the tartaric acid in amounts of from about 20 to about 30 percent. The carbonate compound is employed in amounts of from about 50 to about 60 percent. The binder, preferably polyvinylpyrrolidone, is employed in amounts of from about 0.1 to about 1 percent, and the antifoaming agent in amounts of from about 0.01 to about 0.1 percent by weight. Dyes, if employed, may be added in amounts of from about 0.1 to about 0.5 percent. The amount of solvent suitable for the preparation of the effervescent granulation is about 50 ml. for about every 800 to 900 grams of solids employed.

The Effervescent Formulation for each layer is prepared by first mixing the desired quantities of dry acid and dry alkali metal bicarbonate or carbonate in suitable mixing apparatus, such as a P-K twin-shell liquid-solids blender, Hobart mixer, dough kneader or the like. Preferably, the acids are predried for 16 – 24 hours at 50°C., and the carbonate compound predried to a moisture content of 0.4% or less. Dyes, if employed, may be dry blended with the acid and bicarbonate or carbonate. In a separate container, a suitable amount of binder is dissolved in a suitable alcoholic solvent and an antifoaming agent then is added to the binder solution with stirring. The resulting binder-antifoam alcoholic solution then is added in desired amounts to the blended acid - bicarbonate or carbonate mixture and thoroughly blended therewith. The now wetted and evenly blended granular Effervescent Formulation is then spread out on drying apparatus such as trays, tables, pans and the like and placed in a forced draft oven at 50°C. for a period ranging from about 16 to 24 hours to drive off the alcohol and to reduce the moisture content of the blend to about 0.4% water or less. After drying, the Effervescent Formulation is passed through a No. 14 mesh sieve to obtain a granulation of substantially uniform particle size.

Although the components are similar, the granular Effervescent Formulations for use in the enzyme layer and oxidizing layer are not necessarily identical.

The Enzyme Formulation (for the enzyme layer) preferably contains one or more of the enzymes previously enumerated, the Effervescent Formulation above described, a water-soluble lubricant and optionally, flavorings. It may also contain a dye which is normally added during the preparation of the Effervescent Formulation.

The amount of the enzyme or enzymes to be employed is from about 1.0 to about 6 percent of the total weight of the Enzyme Formulation. The enzyme is in the form of a finely divided powder of about 177 microns or less (i.e., of sufficient fineness to pass through a No. 80 mesh screen). The amount of the Effervescent Formulation is from about 75 to 90 percent of the total weight of the Enzyme Formulation.

The water-soluble lubricant, more fully described in copending Application Ser. No. 482,403 has as components, magnesium lauryl sulfate in the form of a dry powder having an average particle size ranging from about 12 to about 20 microns, preferably about 16 microns and polyethylene glycol polymer in a micronized form and of average molecular weight in the range of from about 6,000 to 20,000. The amount of the spray dried magnesium lauryl sulfate powder may be from about 0.2 to about 0.5 percent and the amount of the micronized polyethylene glycol polymer may be from about 0.5 to about 1.5 percent of the total weight of the Enzyme Formulation. The amount of the flavoring may be up to about 8 percent of the Enzyme Formulation.

The particle size of the various solid components may vary from those which are retained on a No. 20 (840 micron sieve opening) mesh screen to those which pass through a No. 80 mesh screen. While the bulk are of particle size to be retained by No. 40 (420 micron sieve opening) to No. 60 (250 micron sieve opening) screens, it is desirable that the enzyme and flavoring be of finely divided powder not retained by a No. 80 mesh screen. This enhances the rapid dissolution of the enzyme layer.

The Enzyme Formulation is prepared by first blending in a suitable mixing apparatus the granular Effervescent Formulation, enzyme and flavoring, if employed, and thereafter adding the magnesium lauryl sulfate and the polyethylene glycol lubricant components and continuing the mixing until all components are thoroughly blended.

The Active Oxygen Formulation (for the active oxygen layer) contains in addition to one or more of the active oxygen compounds previously enumerated and the granular Effervescent Formulation above described, a surfactant and lubricant component, namely, spray dried magnesium lauryl sulfate powder and micronized polyethylene glycol polymer. The amount of the active oxygen compound in the formulation is from about 55 to about 65 percent of the total weight of the Active Oxygen Formulation. Generally, a mixture of active oxygen compounds is employed. Preferred mixture of active oxygen compounds are sodium perborate monohydrate and potassium persulfate and are employed in amounts of from about 20 to about 30 percent and from about 30 to about 40 percent respectively. The amount of the Effervescent Formulation is from about 35 to about 45 percent of the total weight of the Active Oxygen Formulation. Suitable surfactants include sodium lauryl sulfoacetate, sodium lauryl sulfate, other anionic and non-ionic surfactants which are employed in amounts of from about 0.8 to about 2 percent of the weight of the Active Oxygen Formulation. The amount of the spray dried magnesium lauryl sulfate powder may be from about 0.2 to about 0.5 percent and the amount of the micronized polyethylene glycol polymer may be from about 0.4 to about 1.5 percent of the weight of the Active Oxygen Formulation.

The Active Oxygen Formulation is prepared by first blending in a suitable mixing apparatus the granular Effervescent Formulation, the active oxygen compound or compounds and a surfactant, thereafter adding magnesium lauryl sulfate and polyethylene glycol lubricant components and continuing the mixing until the components are thoroughly blended.

Each of the above formulations is adapted to be fed into the hoppers of a tabletting layer press for tabletting under pressure into layer tablets.

In addition to the choice of suitable formulations, consideration of certain other factors are necessary to assure faster dissolving properties of the enzyme layer: (a) the relative thickness of the layers, (b) the proportion of the effervescent producing composition in each layer and (c) the particle size of certain components in each layer.

In the tablets of the present invention, the enzyme layer, is less than one-half and preferably about one-third of the thickness of the total tablet. This may be achieved by employing less than 50 percent the Enzyme Formulation, and greater than 50 percent of the Active Oxygen Formulation. Preferred amounts are from about 30 to 35 percent of the Enzyme Formulation and correspondingly from about 70 to 65 percent of the Active Oxygen Formulation.

The Effervescent Formulation to be employed in each layer may or may not be identical. However, it is essential that the weight percent of the Effervescent Formulation per total weight of the components of each layer be different. Thus, the amount of the Effervescent Formulation in the enzyme layer is in the range of from about 75 to about 90 percent of the Enzyme Formulation. The amount of the Effervescent Formulation in the active oxygen layer is from about 30 to about 40 percent of the total weight of the components of the Active Oxygen Formulation.

The particle size of the components of the tablet are not uniform. Both layers of the tablet have ingredients of different particle size. Moreover, each layer has a different proportion of ingredients of various particle size. Thus, while it is not critical that the relative amounts of each different particle size be limited, it is essential that the enzyme layer have a larger proportion of the finely divided powder, i.e., powder which would pass through a No. 80 mesh sieve. The amount of the latter to be put in the enzyme layer is in the range of from about 30 to about 50 percent of the total weight of the enzyme layer. The amount of finely divided powder to be incorporated in the active oxygen layer is in the range of from about 20 to about 30 percent of the total weight of the active oxygen layer.

In addition, certain other factors are critical to ensure that the enzyme not be deactivated prematurely. Thus, the content of the active oxygen compound must be controlled. The content of the active oxygen compound is preferably in the range of from about 38 to about 42 percent of the total weight of the tablet. It is important also that excess acids not be employed. The formulations are adjusted so that on dissolution of the tablet, the pH is in the range for optional enzyme activity of the particular enzyme used. In the case of a neutral protease, the optimum pH range is from about pH 6.0 to about pH 7.5. A dye in the enzyme layer may be usefully employed as a timing indicator of cleaning accomplished. Thus, a dye with a fade time of 12 to 15 minutes could be employed to indicate substantial completion of cleaning of the denture. In the tablets of the present invention, a high percent of enzyme activity is retained for more than twenty minutes after dissolution of the tablet.

The formulations prepared as above described are fed into the hoppers of a tabletting layer press for tabletting under pressure into two layer tablets. Generally, from about 25,000 to about 35,000 grams of the formulations are employed for every 10,000 tablets. The compressed layered tablets are then packaged in hermetically sealed packets in a conventional manner. In use, the tablets, when placed in water, dissolve in such a manner that the enzyme layer dissolves within the first 30 to 60 seconds and the active oxygen layer dissolves in about 60 to about 120 seconds. The enzymatic activity proceeds before the concentration of the active oxygen compound has reached a level to inactivate the enzyme. Thus, the denture cleanser tablets of the present invention contain both enzyme and active oxygen compound in which the effectiveness of the enzyme is retained both during storage and use.

The following specific example of a representative enzyme and active oxygen containing layered denture cleanser tablet illustrates the present invention. It is presented for illustrative purposes only and is in no way intended to limit the invention.

EXAMPLE

Formulation for 10,000 Enzyme and Active Oxygen Layered Denture Cleanser Tablets Effervescent Formulation No. 1, an effervescent granular formulation for Enzyme Formulation is first prepared as follows:

a. 1540 g. of dried (16–24 hours at 50°C.) citric acid powder USP, 2390 g. of dried (16–24 hours at 50°C.) tartaric acid powder NF, 26.9 g. of Guinea Green B (green dye, product of Kohnstamm), 1.0 g. of D&C Yellow, No. 10 (yellow dye, product of Kohnstamm) and 4710 g. of dried sodium bicarbonate USP No. 1 (product of Church & Dwight) are mixed together thoroughly to obtain a dry powder blend.

b. 75 g. of polyvinylpyrrolidone (K 29–32) is stirred into 500 ml. of absolute denatured alcohol, 7.5 g. of dimethyl polysiloxane antifoam agent then added thereto and stirring continued to obtain a homogeneous liquid solution of polyvinylpyrrolidone with antifoam dispersed therein.

c. The alcoholic solution is then slowly added with mixing into the powder blend and the mixing continued until a uniform granulation is obtained.

d. The wet granulation is spread on dryer trays and dried at 50°C. in a forced-draft oven for about 20 hours until the moisture content of the mixture has been reduced to an amount no greater than about 0.4 percent.

Effervescent Formulation No. 2, an effervescent granular formulation for the Active Oxygen Formulation is prepared in a similar manner:

a. 1450 g. of dried citric acid powder USP, 2257 g. of dried tartaric acid powder NF and 4260 g. of dried finely powdered sodium bicarbonate USP are mixed together.

b. A solution of 75 g. of polyvinylpyrrolidone (K 29–32) and 7.5 g. of dimethyl polysiloxane in 500 ml. absolute alcohol is prepared as previously described. The alcoholic solution is added to the dry mix and thoroughly blended to obtain a uniform granulation which is then dried as described for the preparation of Effervescent Formulation No. 1.

After drying each of the above granulations is put through a No. 14 mesh sieve on the Stokes oscillating granulator to obtain granulations of uniform particle size.

Each of the foregoing Effervescent Formulations are next blended for the preparation of the Enzyme Formulation and the Active Oxygen Formulation to be employed in the two layers of the tablet in the following manner:

The Effervescent Formulation No. 1 above prepared is thoroughly mixed in a P-K twin-shell solids-liquid blender with 500 g. of protease of 3 anson units (a measure of activity based on tyrosine released from hemoglobin as substrate) and 750 g. of Scalva V-30, 364 (a spray dried mint flavor, product of International Flavors and Fragrance, Inc.). After these components are thoroughly mixed, 25 g. of SIPON MLS Powder (a magnesium lauryl sulfate powder, product of Alcolac Chemical Co.) and 100 g. of micronized Carbowax 6000 (polyethylene glycol polymer, av. m.w. 6,000, product of Union Carbide, Liquid Nitrogen Products) are added and the blending continued for about 15 minutes to obtain a thoroughly blended Enzyme Formulation for tabletting as the enzyme containing green layer.

In a similar manner, Effervescent Formulation No. 2, above prepared is thoroughly mixed with 5550 g. sodium perborate monohydrate, 6890 g. potassium persulfate and 200 g. of sodium lauryl sulfoacetate (a surface active agent). Thereafter, 51.2 g. of SIPON MLS Powder (magnesium lauryl sulfate powder) and 102.5 g. of micronized Carbowax 6000 (polyethylene glycol polymer) are added and the blending continued to obtain Active Oxygen Formulation suitable for tabletting as the active oxygen compound containing white layer.

The blended mixtures are separately placed into feed hoppers of a tabletting layer press. From the hopper, the dry, granular ingredients are measured and fed into the die cavities of the press where they are compacted by the tabletting punches into smooth, compact two layer tablets weighing 3.1 g. each and having a Stokes hardness of between 9 to 14 kg.

The tablets thus prepared are effective in removing oral deposits such as plaque, food particles and stains which tend to accumulate on dentures. The cleaning and polishing properties are seen in the following illustration on operations on stained acrylic plates which serve as models for stained dentures.

The stained acrylic plate models employed are prepared in the following manner:

A food stain coating mixture is prepared from egg yolk and grape juice concentrate, the latter prepared by beating three egg yolks with 6 grams of grape juice concentrate until a smooth mixture is obtained. The mixture is applied to the surface of a roughened acrylic plate and the plates then heated for 2 hours at 160°F. to set the stain.

In determining cleansing properties of the tablets of the present invention, the plates are placed in 180 ml. of tap water at 110°F. and the tablets individually dropped therein whereupon bubbles immediately begin to evolve with complete dissolution of the green enzymatic layer in about thirty seconds and the entire tablet within 120 seconds. Observation of the plates after about 15 minutes shows from 30 to 100 percent stain removal.

The denture cleanser tablet described in the foregoing example merely illustrates one of the preferred combination of ingredients, and other ingredients previously described may be substituted for one of the foregoing or may be included additionally within the limitations previously set forth. Moreover, the amounts by weight of the ingredients in the foregoing preferred combination may be expressed in terms of weight based on the weight of the final tablet as follows:

In the enzyme layer:
1. an enzyme, from about 0.5 to about 10 percent;
2. citric acid powder, from about 4 to about 8 percent and tartaric acid powder, from about 6 to about 10 percent;
3. sodium bicarbonate powder, from about 15 to about 20 percent;
4. dimethyl polysiloxane, from about 0.02 to about 0.1 percent;
5. polyvinylpyrrolidone, from about 0.2 to about 0.8 percent;
6. magnesium lauryl sulfate powder, from about 0.08 to about 0.2 percent, and micronized polyethylene glycol (average m.w. 6000) from about 0.2 to about 0.6 percent.

In the active oxygen layer:
1. sodium perborate monohydrate, from about 15 to about 25 percent; potassium persulfate, from about 20 to about 35 percent;
2. citric acid powder, from about 4 to about 8 percent; and tartaric acid powder, from about 6 to about 10 percent;
3. sodium bicarbonate powder, from about 12 to about 20 percent;
4. sodium lauryl sulfoacetate, from about 0.05 to about 0.07 percent;
5. dimethyl polysiloxane, from about 0.02 to about 0.1 percent;
6. polyvinylpyrrolidone, from about 0.2 to about 0.8 percent;
7. magnesium lauryl sulfate powder, from about 0.15 to about 0.4 percent; and micronized polyethylene glycol (average m.w. 6000), from about 0.2 to about 0.6 percent.

What is claimed is:

1. A water-soluble effervescent layered denture cleanser tablet consisting essentially of
   a. an enzyme layer in an effervescence producing composition and,
   b. an active oxygen layer in an effervescence producing composition
   wherein the enzyme layer is faster dissolving than the active oxygen layer; and wherein
   i. said tablet contains at least one enzyme in an amount of from about 0.5 to 10 percent by weight and at least one active oxygen compound in an amount of from about 38 to 42 percent by weight, said amounts being based on the total weight of tablet,
   ii. in said tablet the enzyme layer is less than one-half and the active oxygen layer more than one-half of the total thickness of the tablet,
   iii. the effervescence producing composition in each layer of said tablet comprises an acid and an alkali metal carbonate compound,
   iv. the amount of said effervescence producing composition to be incorporated in said tablet is for the enzyme layer from about 75 to 90 percent of the weight of the enzyme layer and for the active oxygen layer from about 30 to 40 percent of the weight of the active oxygen layer, and
   v. each layer of said tablet has incorporated therein components in the form of finely divided powder of particle size of about 177 microns or less, the amounts of said powder being, for the enzyme layer from about 30 to 50 percent of the weight of the components of the enzyme layer and for the active oxygen layer from about 20 to 30 percent of the weight of the components of the active oxygen layer.

2. A tablet according to claim 1 wherein in the enzyme layer, the enzyme is at least one selected from the group consisting of protease, alkalase, amylase, lipase, dextranase and mutanase; and in the active oxygen layer, the active oxygen compound is at least one selected from the group consisting of sodium perborate monohydrate, potassium persulfate, sodium carbonate peroxide, diperisophthalic acid and potassium peroxydiphosphate.

3. A water-soluble effervescent, layered denture cleanser tablet consisting essentially of:
   a. an enzyme layer prepared from an enzyme formulation comprising:
      1. from about 1 to 6 percent of at least one enzyme
      2. from about 75 to 90 percent of an effervescent formulation consisting essentially of
         i. from about 35 to 55 percent of at least one acid compound,
         ii. from about 50 to 60 percent of an alkali metal carbonate compound,
         iii. from about 0.01 to 0.1 percent of an anti-foaming agent,
         iv. from about 0.1 to 1 percent of a water-soluble binder, and
      3. a mixture of from about 0.2 to 0.5 percent of magnesium lauryl sulfate and from about 0.5 to 1.5 percent of polyethylene glycol of 6000 average molecular weight as a water-soluble lubricant; and
   b. an active oxygen layer prepared from an active oxygen formulation comprising:
      1. from about 55 to 65 percent of at least one active oxygen compound,
      2. from about 35 to 45 percent of an effervescent formulation consisting essentially of
         i. from about 35 to 55 percent of at least one acid compound,
         ii. from about 50 to 60 percent of an alkali metal carbonate compound,
         iii. from about 0.01 to 0.1 percent of an anti-foaming agent,
         iv. from about 0.1 to 1 percent of a water-soluble binder, and
      3. from about 0.8 to 2 percent of a surface active agent, and
      4. a mixture of from about 0.4 to 1.5 percent of magnesium lauryl sulfate and from about 0.5 to 1.5 percent of polyethylene glycol of 6000 average molecular weight as water-soluble lubricant; and
         wherein in said tablet the enzyme layer is less than one-half and the active oxygen layer is more than one-half of the total thickness of the tablet, and
         wherein each layer of said tablet has incorporated therein components in the form of finely divided powder of particle size of about 177 microns or less, the amounts of said powder being for the enzyme layer from about 30 to 50 percent by weight of the components of the enzyme layer and for the active oxygen layer from about 20 to 30 percent by weight of the components of the active oxygen layer.

4. A water-soluble effervescent, layered denture cleanser tablet according to claim 3, wherein the enzyme is a protease, the acid is a citric-tartaric acid mixture, the active oxygen compound is a mixture of sodium perborate monohydrate and potassium persulfate.

5. A water-soluble, effervescent denture cleanser tablet comprising, by weight based on the weight of the final tablet:
   a. An enzyme layer comprising:
      1. a protease enzyme, from about 0.5 to about 10 percent;
      2. citric acid powder, from about 4 to about 8 percent, and tartaric acid powder, from about 6 to about 10 percent;
      3. sodium bicarbonate powder, from about 15 to about 20 percent;

4. dimethyl polysiloxane, from about 0.02 to about 0.1 percent;
   5. polyvinylpyrrolidone, from about 0.2 to about 0.8 percent;
   6. magnesium lauryl sulfate powder, from about 0.08 to about 0.2 percent, and micronized polyethylene glycol of average molecular weight of 6000, from about 0.2 to about 0.6 percent;
 b. An active oxygen layer containing:
   1. sodium perborate monohydrate, from about 15 to 25 percent; and potassium persulfate, from about 20 to about 35 percent;
   2. citric acid powder, from about 4 to about 8 percent; and tartaric acid powder, from about 6 to about 10 percent;
   3. sodium bicarbonate powder from about 12 to about 20 percent;
   4. sodium lauryl sulfoacetate, from about 0.055 to about 0.065 percent;
   5. dimethyl polysiloxane, from about 0.02 to about 0.1 percent;
   6. polyvinyl pyrrolidone, from about 0.2 to about 0.8 percent;
   7. magnesium lauryl sulfate powder, from about 0.15 to about 0.4 percent; and micronized polyethylene glycol (average molecular weight of 6000), from about 0.2 to about 0.6 percent; and,
 wherein said tablet the enzyme layer is less than one-half and the active oxygen layer is more than one-half of the total thickness of the tablet, and
 wherein said layer of said tablet has incorporated therein components in the form of finely divided powder of particle size of about 177 microns or less, the amounts of said powder being for the enzyme layer from about 30 to 50 percent by weight of the components of the enzyme layer and for the active oxygen layer from about 20 to 30 percent by weight of the components of the active oxygen layer.

* * * * *